United States Patent [19]
Lasner et al.

[11] 4,246,698
[45] Jan. 27, 1981

[54] SUTURE REMOVER

[75] Inventors: Jeffrey I. Lasner, Purchase; Francisco H. Aleixo, Tarrytown, both of N.Y.

[73] Assignee: Laschal Instruments Corp., North Tarrytown, N.Y.

[21] Appl. No.: 59,318

[22] Filed: Jul. 20, 1979

[51] Int. Cl.³ .............................................. B26B 13/00
[52] U.S. Cl. ...................................................... 30/134
[58] Field of Search ........................ 30/134, 135, 124

[56] References Cited
U.S. PATENT DOCUMENTS

| | | | |
|---|---|---|---|
| 2,865,099 | 12/1958 | Blackwood | 30/134 |
| 3,443,313 | 5/1969 | Profy | 30/134 |
| 3,802,074 | 4/1974 | Hoppy | 30/134 |
| 3,922,781 | 12/1975 | Tippy | 30/124 |
| 4,023,270 | 5/1977 | Hellerman | 30/124 |

FOREIGN PATENT DOCUMENTS

| | | | |
|---|---|---|---|
| 17353 | 3/1913 | France | 30/135 |
| 1072449 | 6/1967 | United Kingdom | 30/135 |

Primary Examiner—Jimmy C. Peters
Attorney, Agent, or Firm—Bierman & Bierman

[57] ABSTRACT

A suture remover comprising a shearing portion having a cutting edge, and a blade having a cutting section. The cutting edge and cutting section are adapted to shearingly contact one another by moving toward and away from each other. An element is provided on the shearing portion which has a contact area. The element is affixed to the shearing portion at the end of the element remote from the contact area and has at least one bend in a plane substantially parallel to the plane of the shearing portion and adjacent the end. The contact area overlies the cutting edge or extends beyond it in the direction of the cutting section. At least a part of the cutting section is adapted to be placed between tissue and a suture therein, whereby bringing the cutting section into shearing contact with the cutting edge causes the suture remover to both cut and grip the suture for easy removal.

The means for causing the movement of the cutting edge and cutting section may advantageously be a scissor-like construction or, if desired, a tweezer-like construction.

11 Claims, 3 Drawing Figures

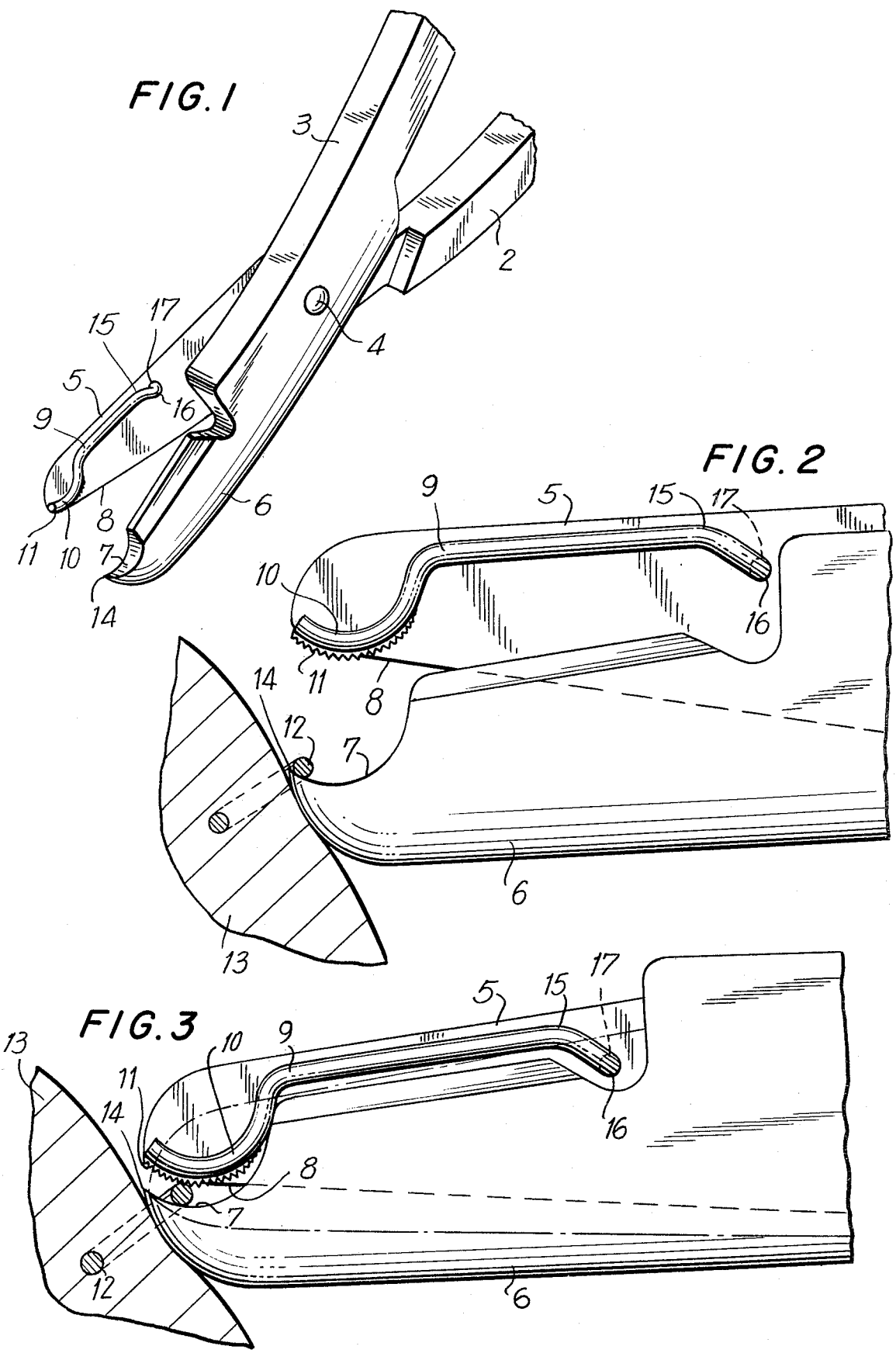

SUTURE REMOVER

The present invention is directed to an improvement in surgical suture removers; more specifically to a suture remover which is capable of both cutting and gripping the suture so that the surgeon can, with one hand, cut the stitches and withdraw the cut thread.

In practicing the present invention there is provided a suture remover of generally scissor-like form. It comprises a first shank pivotally mounted on a second shank at a point intermediate the ends of each of said shanks. One end of each of the shanks is a handle.

The first shank terminates, at its end remote from the handle, in a shearing portion, while the second shank terminates, at its end remote from the handle, in a blade. The blade has a cutting section and the shearing portion has a cutting edge. The cutting section is adapted to shearingly contact the cutting edge when the "scissors" are closed.

An element having a contact area is provided on the shearing portion. The contact area overlies the cutting edge or extends somewhat beyond it in the direction of the cutting section. The cutting section is adapted to be placed between the tissue which has been sutured and the suture itself. Thus, closing the "scissors" brings the cutting section into contact with the cutting edge and causes the suture to be gripped by the contact area and cut by the cutting edge. This permits the surgeon to withdraw the cut suture.

The element is fixed to the shearing portion at its end remote from the contact area. It is a feature of this invention that a bend be provided in the element adjacent the end. The provision of this bend improves the flexing characteristics of the element and prevents or minimizes "bowing" thereof.

In a preferred form of the invention, the bend is in a plane substantially parallel to that of the shearing portion. In an especially preferred form of the invention, there is a second bend in a plane substantially perpendicular to that of the shearing portion and at the end of the element.

It has been found preferable for the contact area to extend slightly beyond the cutting edge. This permits the suture to be first gripped between the cutting section and the contact area, and then cut between the cutting edge and the cutting section.

For best results, it has been found advisable to locate the cutting section adjacent the end of the blade remote from the pivot point. At the same time, it is best that the end be rounded in order to avoid abrading or damaging the tissue.

The contact area advantageously should move in a direction away from the cutting section when pressed by the section and/or the suture. In the most preferred form of the device, this is accomplished by resiliently mounting the element on the shearing portion. Thus, as the scissors are closed, the suture and/or the cutting section exerts a force on the contact area of the element. The resilience of the element permits the area to move so that it no longer extends beyond the cutting edge. The cutting edge can then cut the suture and it remains gripped between the cutting section and the contact area. The surgeon can then remove it with no difficulty.

If desired, the contact area of the elements can be roughened to provide increased friction and improve the grip. Serrations have been found particularly useful for this purpose.

In the accompanying drawings, constituting a part hereof, and in which like reference characters indicate like parts, FIG. 1 is a perspective view of the operative portion of the device;

FIG. 2 is an enlarged fragmentary view showing the device after the suture has been engaged but before it has been gripped; and FIG. 3 is a view similar to that of FIG. 2 subsequent to the gripping of the suture but prior to cutting thereof.

Suture cutter 1 comprises a generally scissor-like configuration having a first shank 2 and a second shank 3. Shanks 2 and 3 are pivotally connected at point 4, and are provided with handles (not shown) at one of their respective ends. First shank 2 and second shank 3 are provided with shearing portion 5 and blade 6, respectively. Blade 6 has cutting section 7 terminating in rounded end 14 at its end remote from pivot point 4. Shearing portion 5 is provided with cutting edge 8 and resilient element 9. Element 9 has contact area 10 adjacent its end remote from pivot point 4. Contact area 10 extends beyond cutting edge 8 in the direction of cutting section 7. In the form of the device shown, contact area 10 is provided with serrations 11 to improve the grip of suture 12.

Element 9 is affixed to portion 5 at end 16 by, for example, soldering or brazing. Adjacent end 16 is bend 15 and second bend 17 is located at end 16. Bend 15 is in a plane substantially parallel to that of portion 5 and second bend 17 is in a plane substantially perpendicular to that of portion 5.

In operation, rounded end 14 is inserted between suture 12 and tissue 13. The scissors are then closed and serrations 11 on contact area 10 grip suture 12 with cutting section 7. Further closing of the scissors causes cutting edge 8, in cooperation with cutting section 7, to cut suture 12. The grip of the suture between contact area 10 and cutting edge 7 is maintained. The surgeon then withdraws the instrument from the body and the cut suture is carried with it.

As can be seen from the foregoing, the use of the device of the present invention makes it difficult, if not impossible, to cut or abrade the tissue while removing the suture. In addition, the entire operation can be carried out with one hand, leaving the surgeon's other hand free. Moreover, the bends 15 and 17 in element 9 permit the desired flexing thereof without undue strain at end 16 and without undesirable "bowing".

In an alternate modification of the present invention, the pivoted shanks of the device can be replaced with a tweezer-like arrangement. The ends of the shearing portion and the blade are connected to one another in a resilient manner at a point remote from the cutting edge and cutting action. This eliminates the need for the pivoted construction and, more importantly, enables the entire instrument to be made much smaller. This decrease in size permits the surgeon, if he so desires, to work very close to the tissue from which the sutures are being removed. This is of particular advantage in the case of eye surgery and similar delicate procedures.

Such changes as would be apparent to the person or ordinary skill in the art may be made without departing from the scope of the invention. For example, the size, shape, and/or configuration of the elements of this device may be altered in order to make the instrument more readily used in particular or specialized portions of the body. The locations of the cutting edge, cutting section, and gripping element may be changed, so long as the device is capable of gripping the suture and maintaining the grip after the suture has been severed.

These and other changes may be made in the invention without departing from the spirit thereof. While only a limited number of embodiments have been expressly disclosed, it is, nonetheless, to be broadly construed and not to be limited except by the character of the claims appended hereto.

What is claimed is:

1. In a suture remover comprising a shearing portion having a cutting edge, and a blade having a cutting section, at least one of said edge and said section being adapted for movement toward and away from the other along a cutting plane for shearing contact with a suture to be cut, an elongated suture gripping element having a contact area and connected to said shearing portion at an end of the element remote from said contact area, said gripping element being substantially planar along its elongation and resiliently deformable for gripping the suture whereby relative movement of said cutting edge and cutting section along said cutting plane for shearing contact with the suture during operative use of the suture remover causes deformation of the gripping element such that its contact area is resiliently moved along said cutting plane and substantially perpendicular to the elongation of the gripping element, said suture gripping element further including at least a bend in the plane of its elongation and adjacent said end remote from the contact area for facilitating the distribution of said deformation of the element between said bend and said end connection of the element during operative use of the suture remover so as to prevent premature deterioration of said connection and thereby extend the useful operational life of the suture remover.

2. In a suture remover according to claim 1, said gripping element further including a second bend substantially at said end thereof and lying in a plane substantially perpendicular to the elongation of said gripping element.

3. In a suture remover according to claim 1, a first and a second shank pivotally connected at a point intermediate their ends and one end of each of said shanks defining a handle, said first shank terminating at an end remote from its handle in said shearing portion and said second shank terminating at an end remote from said handle in said blade so as to form a scissor-like structure of the suture remover.

4. In a suture remover according to claim 1, said contact area normally extending beyond said cutting edge such that in operative use said remover first grips and then cuts the suture.

5. In a suture remover according to claim 1, an end of said blade adjacent said cutting section being rounded.

6. In a suture remover according to claim 3, said cutting section being adjacent an end of said blade remote from said point.

7. In a suture remover according to claim 1, said contact area of the gripping element being adapted to move in a direction away from said cutting section under the urgency thereof during operative use of the suture remover.

8. In a suture remover according to claim 1, said gripping element comprising a wire member.

9. In a suture remover according to claim 1, said plane of elongation of the gripping element substantially corresponding to said cutting plane.

10. In a suture remover comprising a shearing portion having a cutting edge and a blade having a cutting section, at least one of said edge and said section being adapted for movement toward and away from the other for shearing contact with a suture to be cut, and a resilient element on said shearing portion for gripping the suture and having a contact area, said element being elongated along a plane and being affixed to said shearing portion at an end of said element remote from its contact area, and at least a part of said cutting section being adapted to be placed between tissue and a suture therein to be cut whereby bringing said cutting section into shearing contact with said cutting edge causes the suture remover to both cut and grip the suture, the improvement comprising:

at least a bend of less than 90 degrees in said element in the plane of its elongation and adjacent said end at which said element is affixed to the shearing portion, and an elongated, substantially straight portion on said resilient element extending between and spacing apart said contact area and said bend.

11. In a suture remover according to claim 10, a second bend in said element substantially at said end thereof, at least a portion of said second bend lying in a plane substantially perpendicular to the elongation of said element.

* * * * *